United States Patent [19]

Herber et al.

[11] Patent Number: 5,433,793
[45] Date of Patent: Jul. 18, 1995

[54] PREPARATION OF HIGH PURITY D-ALLOSE FROM D-GLUCOSE

[75] Inventors: Raymond R. Herber, Medinah; Gregory F. Maher, Aurora; Edward C. Arnold, Naperville; Thomas W. Lorsbach, La Grange, all of Ill.

[73] Assignee: UOP, Des Plaines, Ill.

[21] Appl. No.: 215,429

[22] Filed: Mar. 22, 1994

Related U.S. Application Data

[63] Continuation-in-part of Ser. No. 99,643, Jul. 30, 1993, abandoned.

[51] Int. Cl.$^6$ ............ C13J 1/06; C07H 1/00; C07H 3/00
[52] U.S. Cl. ............ 127/46.1; 127/46.2; 536/124; 536/127
[58] Field of Search ............ 127/46.1, 46.2; 536/124, 127

[56] References Cited

U.S. PATENT DOCUMENTS

| | | | |
|---|---|---|---|
| 4,029,878 | 6/1977 | Kruse | 536/1 |
| 4,718,405 | 1/1988 | Firth et al. | 127/46.1 |
| 4,815,445 | 1/1989 | Swedo | 127/46.1 |

Primary Examiner—Paul Lieberman
Assistant Examiner—Patricia L. Hailey
Attorney, Agent, or Firm—Thomas K. McBride; Eugene I. Snyder

[57] ABSTRACT

A flow scheme is presented for the production of high purity D-allose from D-glucose. The key reaction is epimerization of D-glucose at C-3 to afford D-allose in per pass yields of at least 7%. The epimerization reaction product is then subjected to concentration, decolorization, and deionization before entering a separation zone, preferably a sorptive separation zone, from which an extract stream enriched in D-allose is obtained.

12 Claims, 1 Drawing Sheet

PREPARATION OF HIGH PURITY D-ALLOSE FROM D-GLUCOSE

CROSS REFERENCE TO RELATED APPLICATION

This application is a continuation-in-part of my application, U.S. Ser. No. 08/099,643, filed Jul. 30, 1993, now abandoned, all of which is hereby incorporated by reference.

BACKGROUND OF THE INVENTION

Present dietetic needs, predilections, and perceptions have led to the increased use of replacement sweeteners as a substitute for the "natural" sugars, including sucrose and fructose. Although such replacement sweeteners are under continual review for their long term physiological affects, their demand has grown unabated. Accompanying their growth as a commercial product area with substantial economic impact has been a renewed emphasis on discovering and supplying new replacement sweeteners.

Among its characteristics, the ideal replacement sweetener would be noncaloric, noncariogenic, without detrimental physiological effects, and usable by diabetics. These requirements would be met if a sweetener were not metabolized by humans and by flora which are found in the mouth and intestinal tract, and if it were without effect on any internal organ. The ideal sweetener should be excreted in the same form as when ingested. Another desirable feature is that it have bulking properties similar to sucrose and browning ability so that it can be substituted for table sugar (sucrose) and dextrose in many formulations.

Recently, attention turned toward the L-sugars as desirable replacement sweeteners. It has been known since at least 1946 that L-fructose is sweet (M. L. Wolfrom and A. Thompson, *J. Am. Chem. Soc.*, 68, 791,793 (1946)), and since at least 1890 that L-fructose is nonfermentable (E. Fischer, *Ber. Deutsch. Chem. Ges.*, 23, 370,389 (1890)), hence not metabolized by microorganisms generally metabolizing D-sugars. A reasonable, although not necessarily correct, inference is that it also is not metabolized by humans. Unfortunately, the early hopes and expectations raised for L-hexoses were not corroborated by experimental observations, leading ultimately to a search for other "ideal" sweeteners.

Even though one might have expected the sweetness of the D-hexose monosaccharides to have been thoroughly investigated previously, this is not the case. Among the aldol hexoses D-glucose is of course widely known to be sweet, and D-gulose is reported to be a sweet syrup (Merck Index, 10th Edition, page 659 (4458)). More recently D-galactose has been found to be sweet (Shallenberger and coworkers, *Nature*, 221, 555 (1969)). Although mannose also is reported to be sweet, the situation is somewhat complicated by the fact that its two enantiomers appear to have distinctly different organoleptic properties, with $\beta$-D-mannose actually being bitter: G. G. Birch and coworkers, *J. Sci. Fd. Agric.*, 21, 650 (1970); R. S. Shallenberger and coworkers, *J. Food Sci.*, 30, 560 (1965); "Sugar Chemistry", R. S. Shallenberger and G. G. Birch, page 117, The AVI Publishing Company, Inc., (1975). It should be apparent that a bitter taste is an objectionable organoleptic property in a substance contemplated for use in foods as a sweetener or sweetener replacement. Of the ketohexoses the sweet taste of D-fructose is common knowledge, and more recently D-tagatose has been reported to be sweet. See U.S. Pat. No. 4,786,722 and references cited therein.

The metabolism of D-glucose and, to a lesser extent D-galactose, is relatively well studied, but reports on other D-aldohexoses are sparse. Fischer and Thieffelder, op. cit. reported that D-mannose was readily fermented by most, but not all, yeasts they were tested against, but that D-talose was not fermented by any of the twelve. Of the D-ketohexoses the metabolic fate of D-fructose is well documented. Recently the patentee in U.S. Pat. No. 4,786,722 reported that most of D-tagatose given orally to rats was recovered in the feces. However, the lack of detailed experimental data make the qualitative statement of results difficult to evaluate.

Recently the patentees of U.S. Pat. No. 4,963,382 found that both D-talose and D-allose are sweet, that neither has any strong objectionable taste characteristics, and that neither is substantially metabolized in rats. There also are strong indications that at least D-allose is non-cariogenic. Our findings make possible a means to provide reduced calorie sweetening to foods while mimicking other effects of sucrose in foodstuffs, effects to which society has become accustomed through the ages. Thus it appears that D-allose in particular may serve as a reduced-calorie bulking sweetener which can be substituted for sucrose and dextrose in a wide variety of food formulations without necessitating any large changes in recipes, which can be expected to be metabolized in humans to only a small extent, if at all, which undergoes a browning reaction when heated or baked, and which is readily crystallized. Crystallinity often is needed to impart the correct mouth feel to a given foodstuff.

D-allose also holds interest as a component of new pharmaceuticals, especially antiviral agents where one component may be an aldohexose or a derivative thereof. Consequently there is a need for preparing high purity D-allose in quantities not previously possible.

SUMMARY OF THE INVENTION

A purpose of our invention is to provide a commercially feasible preparative route to high purity D-allose, especially in crystalline form. An embodiment comprises epimerizing the D-glucose in an aqueous feedstock, concentrating the epimerized reaction product containing D-allose to a level of 50–60% dry solids while recovering at least 90% of the D-allose in the epimerization effluent, removing the color bodies and ionic materials from the concentrated epimerized product, subsequently separating the allose into a stream in which at least 80% of the dry solids is D-allose and at least 90% of all monosaccharides present is D-allose, and returning the raffinate to the aqueous glucose feedstock used for the epimerization zone. One aspect to the invention accompanying high by-product formation is to remove as a bleed stream no more than 25% of the raffinate. In a specific embodiment epimerization is effected by molybdate. In a still more specific embodiment the epimerization is effected by a soluble molybdate. In another embodiment the epimerization is effected by a supported molybdate. In yet another specific embodiment separation is practiced in a sorptive separation zone which may be either a fixed bed or a moving sorbent bed system. Other embodiments and purposes will become clear from the following description.

DESCRIPTION OF THE INVENTION

Figure 1:
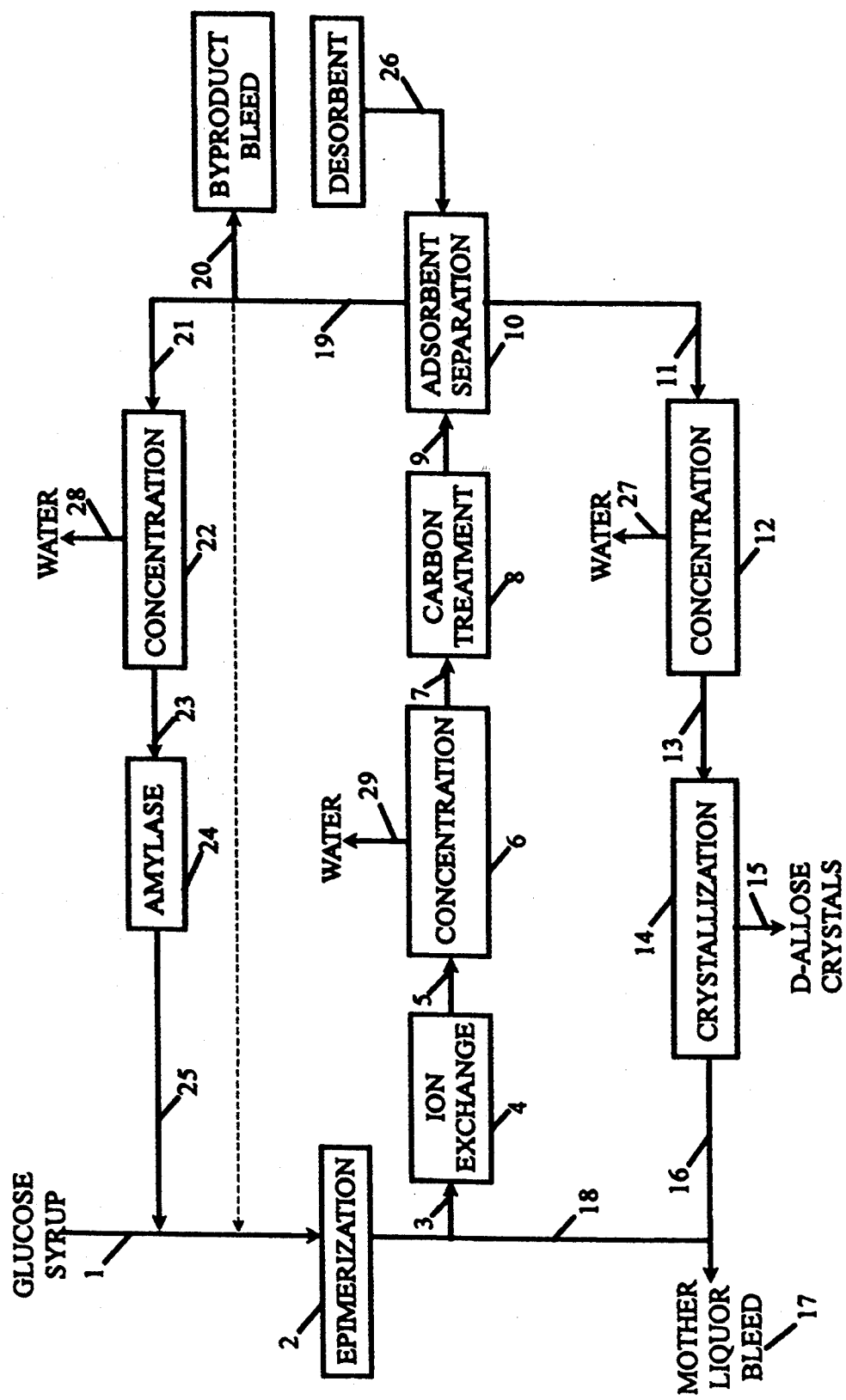
FIG. 1 is a process flow scheme for the conversion of D-glucose to D-allose.

Although our invention is depicted in the flow scheme of FIG. 1 and is described in greater detail within, we can briefly summarize our method of preparing D-allose as follows. Our scheme basically involves one chemical reaction and one separation, but each has stringent requirements and important limitations. The reactive portion of our flow scheme is the epimerization of glucose to allose. The remainder of our flow scheme is related to the separation of D-allose formed during epimerization, ultimately with the production of a stream where D-allose represents at least 50% of all dry solids, and preferably at least 80% of all dry solids, and at least 90% of the monosaccharides present. This stream is readily utilized as a crystallizer feedstock from which crystallization of D-allose of >99% purity can be routinely performed. Although a crystallization stage is not a necessary component of our invention, we stress that the product of our invention is most usually used as a source of crystalline D-allose.

Our process uses as a feedstock an aqueous solution of an aldohexose, or mixture of aldohexoses, which can be epimerized to D-allose. The most common such aldohexose is D-glucose; although D-mannose as well as several relatively rare aldohexoses may also be utilized in principle their availability and price makes their deployment unfeasible. As a practical matter D-glucose is by far the most commercially attractive feedstock. As will be apparent, because of the large amount of material recycled in our process the mixture entering the epimerization zone is a mixture of D-glucose and the several products normally found in the recycle stream. However, it should be equally apparent that D-glucose is the raw material for our process; our overall process is the conversion of D-glucose to D-allose even though material entering the epimerization zone is a mixture of several aldohexoses participating in subsequent reaction. For convenience of exposition we shall refer to the feedstock as one of D-glucose with the clear understanding that it is a mixture of aldohexoses which enters and reacts in the epimerization zone.

Although the source of D-glucose is not per se important to the success of our invention, this is not to say that the D-glucose source is without effect. At one extreme the aqueous feedstock may contain pure D-glucose. This situation represents the highest cost scenario but also prevents the fewest complications from extraneous materials introduced into the glucose feedstock. It also may be noted at this point that even the use of relatively pure D-glucose leads to the formation of abundant quantities of side products arising when the operating conditions of several unit processes uses temperatures in excess of 120° C. It is well known that monosaccharides generally, as well as disaccharides and higher polysaccharides, are heat labile and undergo various thermal reactions, especially base-catalyzed degradative oxidation reactions, at temperatures in excess of 100° C.

At the other extreme one may use as the glucose feedstock an unpurified starch hydrolysis stream. Such a feedstock has the virtue of being quite cheap but also contains a number of components which are chemically unreactive and which may accumulate in the system. Where this occurs it is necessary to modify the flow scheme to accommodate the accumulation of such unreactive materials. As a practical matter saccharified corn starch as available from the corn wet milling industry is a quite acceptable and economical feedstock.

Although the aldohexose content of the feedstock entering the epimerization zone is unimportant in principle, it is of great practical importance in affecting the economics of the process. The feedstock ought to contain at least 5% dry solids and preferably contains between about 5 and about 30% dry solids as glucose (and other aldohexoses from the recycle stream). Higher dry solids contents are preferred in the practice of our invention in order to minimize the size of the separation stage; however, vide infra.

The aqueous feedstock is introduced into an epimerization zone which effects the epimerization of, e.g., glucose at C-3 to form D-allose.

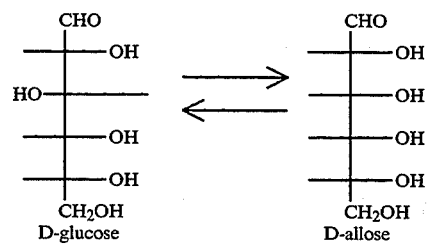

Any means of epimerizing D-glucose to D-allose may be used, although naturally an agent which does so with maximum selectivity and extent of conversion is to be favored. The extent of side product formation also needs to be taken into account in evaluating a means of effective said epimerization. One acceptable means is to use molybdenum as an epimerization catalyst in either a soluble or insoluble form; see U.S. Pat. Nos. 4,718,405 and 4,815,445. Not only is it desirable to have the epimerization proceed as selectively as possible and with high yield, it is quite desirable to perform the epimerization at as low a temperature as possible. As indicated above, many side reactions occur at temperatures in excess of 100° C. Some of these reactions are degradative and form C4 and C5 products which represent irreversible losses in the system. Among other degradation pathways may be mentioned dehydration and furfural formation.

As an example of epimerization, one may use water-soluble molybdate under somewhat acidic conditions. Although it is not believed that the nature of the soluble molybdate is important in influencing the course of the epimerization of D-glucose to D-allose, we have determined that ammonium molybdate is a quite effective molybdate source. However, ill needs to be emphasized that other soluble molybdates also may be used in the practice of our invention, where such molybdates include sodium and potassium molybdate as exemplary of the soluble molybdates of our invention.

The soluble molybdate may be present at concentrations between about 0.05 and about 0.14 weight percent although the successful practice of our invention does not appear to be dependent upon molybdate concentration. It is desired that the pH of the solution be between about 2.5 and about 4.5. The nature of the acid used to achieve the requisite pH is largely a matter of choice, but the use of a dilute aqueous acetic acid solution as solvent has been found to be quite effective in minimizing color formation accompanying epimerization of D-glucose to D-allose, especially in the temperature range of 100° up to about 135° C. Insoluble molybdate also can be utilized in effecting the epimerization as taught in U.S. Pat. No. 4,815,445. We have found that the dry solids content of the feedstock to the epimerization zone affects byproduct formation, with a lower dry solids content being identified with lower byproduct formation. However, commercially one desires to operate at the highest feasible dry solids level.

The reaction time will depend sensitively upon epimerization conditions, especially epimerization temperature. It is quite desirable to optimize the time for maximum D-allose yield while minimizing degradation products. It is desired to conduct the epimerization under reaction conditions and for a time sufficient to afford at least 7% D-allose, and preferably under conditions affording at least 10% D-allose. It also is desired that at least 90% of the aldohexoses entering the epimerization zone be recovered in the effluent from the epimerization zone, preferably at least 95%, and it is still more preferable that at least 97% of the aldohexoses is recovered.

The influent to the separation zone desirably contains from 50 to about 60% dry solids. Since the effluent from the epimerization zone contains considerably lower dry solid content, it is necessary to concentrate the effluent prior to its entry to the separation zone. Epimerization usually generates color bodies and it also is desirable to remove, in part or in whole, such color bodies prior to separation. Since materials with a high ionic strength also interfere with the separation, their removal or reduction to a lower level than usually is found in the epimerization effluent also is performed prior to separation. The triad of operations performed on the epimerization effluent must lead to a colorless, or nearly so, product having 50–60% total dry solids and with a conductivity no more than about 40 microsiemens. The sequence of operations—concentration, decolorization, and deionization—is largely a matter of choice provided the desired result is attained. For convenience only we shall describe our invention as if the sequence were concentration, decolorization, and deionization, but it should be recognized this is chiefly for expository convenience. It would appear that deionization prior to concentration is advantageous.

Consequently, effluent from the epimerization zone is passed to a concentration zone which normally consists of an evaporator. In the evaporation zone water is removed at reduced pressure and using somewhat elevated temperatures. Evaporation of the epimerization reaction product to between 50–60% total dry solids may be accomplished at 25–28 inches Hg vacuum at a temperature no higher than 140° F. (60° C.), desirably no higher than 135° F., since there seemed to be significant carmelization of aldohexoses at higher temperatures. The optimum temperature is that at which aldohexose loss due to thermal degradation is minimized, ideally to no loss at all. The pressure used is a matter of choice, although clearly the lower the pressure the lower the temperature required for evaporation. What is necessary is to perform the concentration so as to recover at least 90% of the aldohexose product in the C-3 epimerization zone.

After the dry solids content of the C-3 epimerization effluent has been increased to a level of about 50 to about 60 weight percent the resultant concentrated stream enters a color removal zone to remove color bodies. In the most usual case this is merely a bed of charcoal or some other form of activated carbon which preferentially adsorbs highly colored materials which may be present in the concentrated stream without substantial adsorption of D-allose. The color removal zone normally is run at a temperature between about 20° and about 70° C., preferably under 60° C. to minimize allose degradation. Conditions are chosen preferably to attain aldohexose recoveries of at least 97%. The reduction of color usually is complete, with the effluent from the carbon treatment being water white or reasonably close thereto.

At this point the concentrated stream containing D-allose may contain substantial amounts of high ionic strength substances which need to be removed prior to the stream being sent to the separation zone. Removal is most conveniently effected by passing the concentrated stream through an ion exchange column(s) of sufficient size and type to reduce the conductivity of the effluent from the ion exchange column to no more than about 40 microsiemens (mhos). Both anion and cation exchange resins are desirably employed to reduce the content of charged materials to as low a level as practicable, with no special preference for any particular resin within either class. It is somewhat preferred that the resin be food grade. Ion exchange frequently is employed at a temperature no higher than about 40° C. since this represents the maximum operating temperature of many ion exchange resins.

We note again that although the preparation of decolorized, deionized concentrate has been described as concentration preceding decolorization preceding deionization, the sequence is largely a matter of choice. Whether a particular sequence of operations is preferable seems to be unsettled. What is settled is the need to recover at least 90% of the aldohexose contained in the C-3 epimerization zone effluent after a combination of concentration, deionization, and decolorization.

The concentrated stream from which color bodies and ionic materials have been removed then is sent to a separation zone where D-allose is separated and removed from other components present in the concentrated stream. A preferred separation zone is a sorptive separation zone, that is, one where an adsorptive separation process is used to separate D-allose from, for example, other monosaccharides, polysaccharides, and degradation products present in the concentrated stream. We particularly prefer as a sorptive separation zone one where the adsorbent preferentially and selectively adsorbs D-allose while permitting other components in the concentrated stream to pass through the separation zone unchanged. In practicing our invention according to this preferred mode the concentrated stream containing D-allose and other components is passed over an adsorbent which selectively adsorbs D-allose and most other components are permitted to pass through the zone unchanged and are collected in a raffinate stream. The flow of the feedstock is stopped periodically, the adsorbent zone is flushed to remove nonadsorbed materials, and adsorbed D-allose is desorbed from the adsorbent by flowing a desorbent through the adsorbent and collecting as an extract D-allose in the desorbent effluent. The desorbent contemplated to be most commonly employed in the practice of this invention is water, although aqueous alcohols, especially aqueous ethanol, may be employed under suitable conditions.

Sorptive separation may be practiced in many variants, as for example in a fixed bed or moving sorbent bed system. Within the latter are such variants are countercurrent moving bed, simulated moving bed countercurrent flow, and cocurrent high efficiency simulated moving bed system. These and other variants are well known in the art and will not be further discussed here. See, for example, U.S. Pat. No. 4,837,315 for an extended discussion of sorptive separation practice complete with voluminous references thereto.

Any adsorbent which preferentially adsorbs D-allose relative to the other components in the stream may be used. Such adsorbents include ion exchange resins of either the gel or macroreticular type, although a macroreticular type may have a lower capacity for D-allose. Cation exchange resins in the calcium form appear to work well. Other adsorbents which, at least in principal, could be employed in the practice of this invention include aluminas and zeolites, especially dealuminated zeolite Y, although the limited aqueous stability of the zeolites relative to the ion exchange resins make the latter more attractive materials as adsorbents. Food grade materials are preferred for reasons which should be clear. For good adsorption and desorption rates it is desirable to have the separation temperature as high as possible, but not so high as to induce thermal degradation of D-allose. Temperatures between 40° and 65° C. usually are used. The pH of the feed to the separation is between 6 and 7, with the solids content at least about 50%.

It is necessary to conduct the D-allose separation such that the extract affords D-allose in an amount corresponding to at least 50% of the total contained solids, preferably to at least 80% of the total solids contained therein, and where the D-allose corresponds to at least 90% of the monosaccharides contained in the extract. It is even more preferable that D-allose be present in an amount such that it constitutes at least 95% of all monosaccharides present. In the case where the extract is used per se., i.e., as a syrup, then it is only necessary that the D-allose constitute at least 80% of the monosaccharides present. However, it is contemplated that in most instances the extract will be sent to a crystallizer for the production of crystalline D-allose, generally after concentration by evaporation, under which circumstances a D-allose content of at least 90% of all monosaccharides is the preferred mode of practice. Recovery of at least 95% of the D-allose in the extract is required, and a recovery of at least 97% is preferred.

The raffinate from the separation zone is then recycled to the glucose-containing feedstock. Where the initial glucose-containing feedstock contains a substantial amount of disaccharides, trisaccharides, and higher polysaccharides, these are advantageously treated with an amylase prior to being recycled to the glucose-containing feedstock so that such materials do not accumulate in the system. Amylases constitute a group of enzymes which degrade starch and glucose oligomers (i.e., disaccharides, trisaccharides, and higher polysaccharides) to glucose itself. The amylases show a variety of activity characteristics with respect to degree of polymerization, and the choice of amylase used in raffinate treatment will depend upon the components present in said raffinate. Clearly, the choice of amylase will be judiciously made so as to effect the maximum degradation of glucose polymers to the monomer.

Whether or not the raffinate is treated with an amylase prior to being returned to the glucose-containing feedstock it may be necessary to divert an amount from something greater than zero up to perhaps as large as 25% of the raffinate stream as a bleed stream which is removed from the system. This may be necessary in order to prevent the accumulation of materials such as degradation products of various monosaccharides, extraneous protein which may be introduced in a glucose-containing feedstock, and sugars which are not degraded by an amylase to a reactive species. Of course it is desirable to minimize this bleed stream in order to minimize the losses incurred in the system, but it also is desirable to have a sufficiently large bleed stream to prevent the accumulation of undesirable materials which otherwise would interfere with various unit processes being undertaken in our invention.

As ought to be clear from the foregoing description, many variants of our invention are possible. One variant of the process which is our invention is depicted in FIG. 1. The glucose feedstock 1 enters the epimerization zone 2 where glucose is epimerized to allose at least to the extent of 7%, and preferably to a level greater than about 10%. The glucose feedstock itself contains at least 5 weight percent glucose and it is preferred that the dry solids content be between about 10 and about 30 weight percent, with some preference being toward the higher range. Effluent from the epimerization zone is removed and contains at least 90% of the aldohexoses entering said zone. It is preferred that at least 95% of the aldohexose in the feed to the epimerization zone be recovered.

The effluent 3 from the epimerization zone must then be subjected to the operations of decolorization, concentration, and deionization, but within this triad there is flexibility as to the particular sequence employed. More particularly, the effluent from the epimerization zone may be sent to a decolorization zone, a concentration zone, and a deionization zone in any sequence, although variants where deionization precedes concentration appear somewhat advantageous. Thus, epimerization effluent 3 in one variant is sent to a deionization or ion exchange zone 4 where ionic materials are removed to the extent that the effluent 5 from the ion exchange zone has a conductivity no greater than about 40 microsiemens.

Effluent 5 from the ionization zone is then concentrated in zone 6, generally by evaporation under as mild conditions as are feasible to minimize degradation of saccharides present in the epimerization effluent, at a temperature no greater than about 140° F., preferably not more than 135° F., at a pressure of 25–28 inches Hg. Water is removed as stream 29, and the dry solids content of stream 7 resulting from concentration is between 50 and 60%. In the variant shown, the concentrate from zone 6 is then sent to a decolorization zone 8, where color bodies present in the concentrate are reduced. Most generally the decolorization zone is merely a bed of charcoal operated at a temperature of about 20°–70° C., preferably under 60° C., and most often in the range of 40°–60° C.

The deionized, decolorized, and concentrated stream 8 is then conducted to the separation zone 10 where D-allose is preferentially adsorbed on a solid adsorbent bed. The resulting D-allose extract 11 contains D-allose in an amount corresponding to at least 50 weight percent, preferably to at least 80 weight percent, of total solids and at least 90 weight percent of all monosaccharides. Most generally the extract stream 11 is further concentrated at a temperature preferably under 130° F. to a dry solids content of at least 75 weight percent prior to its being sent to a crystallizer 14 from which pure crystals of D-allose may be obtained. The chief use of extract stream 11 is as a feedstock for production of crystalline D-allose, although it is also possible to concentrate extract stream 11 and use the syrup per se. Although stream 11 needs to contain D-allose in an amount corresponding to at least 90 weight percent of all monosaccharides present, it is more desirable that 11 contain D-allose in an amount from 90 up to about 95% of the monosaccharides present.

The raffinate 19 from the separation zone is then concentrated in zone 22 sent to an amylase zone 24 where unbranched disaccharides, trisaccharides, other oligomers and starch hydrolysis products are further hydrolyzed to the monosaccharides prior to being recycled to the glucose feedstock stream. The effluent 25 from the amylase zone preferably contains primarily monosaccharides as well as accumulated glucose degradation products which have been formed in various stages of our process. To prevent the accumulation of these degradation products and other materials which tend to accumulate in the system, such as extraneous proteins, a bleed stream 20 may be withdrawn prior to the raffinate stream being recycled to the glucose feedstock. Alternatively, the bleed stream may be placed prior to the amylase zone. This bleed stream constitutes something more than 0% and may constitute as much as 25% of the total raffinate stream. The exact amount of the bleed stream withdrawn will depend upon the amount of degradation products accumulating in the recycle as well as the tolerance and capacity of the adsorbent with respect to these degradation products, and of necessity will be determined by the specific process operating conditions.

We previously mentioned that the chief use of extract stream 11 is as a feedstock for crystallizer 14. From the crystallizer 14 one can readily obtain crystalline D-allose in stream 15 at a purity of at least 99%. The mother liquor 16 is combined with the epimerization effluent stream in order to utilize glucose most efficiently. A bleed 17 may be taken from the mother liquor prior to its combination with the epimerization effluent stream.

The following examples merely illustrate our invention and are not intended to limit it in any way thereby.

EXAMPLE

Epimerization of glucose. A solution containing 800 g crystalline glucose, 15 g of ammonium molybdate, and 48 g of glacial acetic acid with sufficient water to make 8 liters was held at 130° C. and 25 psig for 165 minutes to afford an epimerization mixture containing glucose, altrose, mannose, and allose. The epimerization reaction mixture contained at least 7% D-allose and generally contained between about 9.5 and about 10.5 weight percent D-allose on a dry solids basis.

Concentration of the epimerization reaction product. Typically the epimerization reaction product was treated with the decolorizing agent prior to concentration in the evaporator, although an argument may be made for carbon treating after concentration. Most often this was done by passing the product mixture over a bed of activated carbon that was heated to 60° C. This treatment usually turned the solution from black to something close to water white. The epimerization reaction product was then concentrated to a brix of 50-55. This was performed by evaporating water under a vacuum of 24″ Hg at a temperature not exceeding 60° C. The extent of degradation products seemed to increase appreciably with evaporation temperature and it was found advantageous to keep the temperature in the evaporators no more than about 60° C.

Ion exchange of concentrated epimerization reaction product. An anion and cation exchange resin was used in series to reduce the conductivity of the epimerization reaction product to 40 microsiemens or less. The anion exchange resin was CS-2 from Culligan (food grade), a strongly basic gel type styrene-divinylbenzene resin converted in a column to the hydroxide form according to a procedure provided by the manufacturer. The hydroxide form was washed well with deionized water prior to usage. The cation exchange resin was CH-1 from Culligan (food grade) and was a strong acid, gel type 8% crosslinked styrene-divinylbenzene. The resin was converted to the H+ form by the manufacturer's recommended procedure, then washed-well with deionized water. Ion exchange was conducted at 40° C.

Separation of D-allose. The separation was performed using a simulated moving bed technique (SORBEX ™ process); see, e.g., U.S. Pat. No. 4,837,315. The adsorbent used was ADS-255 (from UOP, Des Plaines, Ill.) in the calcium form, and the desorbent was deionized water, with the separation performed at a temperature no greater than 60° C. to avoid allose degradation.

Recycle of raffinate. The amount of the raffinate removed through the bleed stream depends upon the extent of carbohydrate degradation occurring during epimerization, and while not an absolute necessity is a highly preferred embodiment. Generally the bleed is between about 0.1 up to as high as about 25% of the raffinate, although economic considerations dictate as low a bleed as possible. The remainder of the raffinate is sent to an immobilized amyloglucosidase column to degrade the glucose polymers to glucose, and the product combined with fresh glucose feedstock.

What is claimed is:

1. A method of preparing D-allose from D-glucose comprising:
  a) introducing to a C-3 epimerization zone an aqueous feedstock comprising D-glucose and other aldohexoses from the recycle stream of f), said feedstock containing at least 5 weight percent total aldohexoses;
  b) converting the aldohexoses in said feedstock in the C-3 epimerization zone to produce D-allose in an amount of at least 7 weight percent of all aldohexoses present;
  c) recovering from the C-3 epimerization zone an effluent containing at least 90% of the aldohexoses entering said zone;
  d) preparing from the C-3 epimerization zone effluent a decolorized concentrated stream having a dry solids content from about 50 to about 60 weight percent with recovery of at least 90% of the aldohexose, and with a conductivity of not more than 40 microsiemens to afford a separation feed stream;
  e) introducing the separation feed stream into a separation zone whereby D-allose is separated from other monosaccharides present in said separation feed stream to afford an extract enriched in D-allose and a raffinate depleted in D-allose, where said extract contains D-allose in an amount corresponding to at least 50 weight percent of total solids and at least 90 weight percent of all monosaccharides;
  f) removing from 0 up to 25% of the raffinate as a bleed stream and recycling the remainder of the raffinate as a recycle stream to the C-3 epimerization zone; and g) treating the raffinate with an amylase prior to being recycled to the C-3 epimerization zone.

2. The method of claim 1 where said feedstock contains from about 5 up to about 30 weight percent aldohexoses.

3. The method of claim 1 where at least 10 percent of the aldohexoses are converted in the epimerization zone to D-allose.

4. The method of claim 1 where at least 97 percent of the aldohexoses entering the epimerization zone is recovered.

5. The method of claim 1 where from 90 up to about 95 percent of the monosaccharides in the extract are D-allose.

6. The method of claim 1 where the extract contains D-allose in an amount corresponding to at least 80 weight percent of total solids.

7. The method of claim 1 further characterized in that the D-allose is crystallized from said extract to afford crystalline D-allose of at least 99% purity.

8. The method of claim 1 further characterized in that the extract is conducted to a crystallizer zone, which affords crystalline D-allose of at least 99% purity and a mother liquor which is recycled to said C-3 epimerization zone effluent.

9. The method of claim 1 further characterized in that the conductivity of not more than 40 microsiemens is obtained by ion exchange.

10. The method of claim 9 where the separation feedstream which is a decolorized concentrated stream having a dry solids content from about 50 to about 60 weight percent with recovery of at least 90% of the aldohexose, and with a conductivity of not more than 40 microsiemens is prepared via decolorization and ion exchange which precedes concentration.

11. The method of claim 9 where the separation feedstream which is a decolorized concentrated stream having a dry solids content from about 50 to about 60 weight percent with recovery of at least 90% of the aldehexose, and with a conductivity of not more than 40 microsiemens is prepared via ion exchange which precedes decolorization and concentration.

12. The method of claim 9 where the separation feedstream which is a decolorized concentrated stream having a dry solids content from about 50 to about 60 weight percent with recovery of at least 90% of the aldehexose, and with a conductivity of not more than 40 microsiemens is prepared using the operations of ion exchange, concentration and decolorization in sequence.

* * * * *